United States Patent [19]

Schmidt et al.

[11] 4,167,570

[45] Sep. 11, 1979

[54] 2-METHYL-6-ALKYL-11-AMINOALKYL-6,11-DIHYDRO-5H-PYRIDO(2,3-B)(1,5)BENZODIAZEPIN-5-ONES AND SALTS THEREOF

[75] Inventors: Günther Schmidt; Sigfrid Püschmann; Günther Engelhardt, all of Biberach, Fed. Rep. of Germany

[73] Assignee: Boehringer Ingelheim GmbH, Ingelheim am Rhein, Fed. Rep. of Germany

[21] Appl. No.: 837,578

[22] Filed: Sep. 28, 1977

[30] Foreign Application Priority Data

Sep. 30, 1976 [DE] Fed. Rep. of Germany ....... 2644121

[51] Int. Cl.² ..................... A61K 31/55; C07D 471/04
[52] U.S. Cl. .............................. 424/256; 260/239.3 T; 424/250; 424/248.54; 424/267
[58] Field of Search ................. 260/239.3 T; 424/263, 424/248.54, 250, 256

[56] References Cited

FOREIGN PATENT DOCUMENTS

| | | | |
|---|---|---|---|
| 2424811 | 12/1975 | Fed. Rep. of Germany .... | 260/239.3 T |
| 60439 | 7/1970 | Poland ............................ | 260/239.3 T |
| 60440 | 7/1970 | Poland ............................ | 260/239.3 T |

OTHER PUBLICATIONS

Chemical Abstracts, vol. 80, Item 59921(f), 1974, Abstracting Nantka-Namirski et al., "vol. J. Pharmacol. Pharm", (1973), vol. 25, No. 5, pp. 441-445 (1973).

*Primary Examiner*—Alan L. Rotman
*Assistant Examiner*—Robert T. Bond
*Attorney, Agent, or Firm*—Hammond & Littell

[57] ABSTRACT

Compounds of the formula

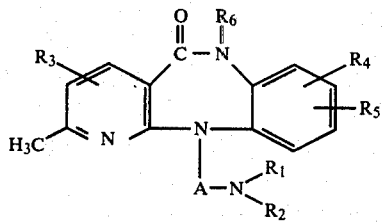

wherein
  $R_1$—is hydrogen, alkyl of 1 to 6 carbon atoms or benzyl;
  $R_2$—is alkyl of 1 to 6 carbon atoms, cycloalkyl of 5 to 7 carbon atoms or, together with $R_1$ and the adjacent nitrogen atom, pyrrolidino, piperidino, hexamethyleneimino, morpholino or N'-methylpiperazino, where each of the heterocycles may have one or two alkyl of 1 to 3 carbon atoms or one or two methoxy substituents attached thereto;
  $R_3$,—$R_4$ and $R_5$ are each hydrogen or methyl;
  $R_6$—is alkyl of 1 to 4 carbon atoms; and
  A—is alkylene of 2 to 4 carbon atoms;

and non-toxic, pharmacologically acceptable acid addition salts thereof; the compounds as well as their salts are useful as bronchospasmolytics and bronchosecretolytics.

5 Claims, No Drawings

2-METHYL-6-ALKYL-11-AMINOALKYL-6,11-DIHYDRO-5H-PYRIDO(2,3-B)(1,5)BENZODIAZEPIN-5-ONES AND SALTS THEREOF

This invention relates to novel 2-methyl-6-alkyl-11-aminoalkyl-6,11-dihydro-5H-Pyrido[2,3-b][1,5]Benzodiazepin-5-ones and non-toxic acid addition salts thereof, as well as to various methods of preparing these compounds.

THE PRIOR ART

Analogous pyridobenzodiazepinones, but which are unsubstituted in the 2-position, are disclosed in German Offenlegungsschrift No. 2,424,811, published Dec. 18, 1975. The prior art compounds are said to have bronchospasmolytic properties, and some of them also bronchosecretolytic properties.

THE INVENTION

More particularly, the present invention relates to a novel class of pyridobenzodiazepinones represented by the formula

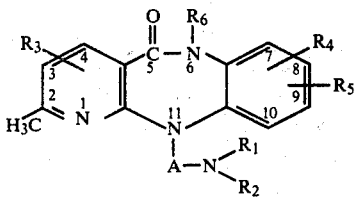

wherein
$R_1$—is hydrogen, alkyl of 1 to 6 carbon atoms or benzyl;
$R_2$—is alkyl of 1 to 6 carbon atoms, cycloalkyl of 5 to 7 carbon atoms or, together with $R_1$ and the adjacent nitrogen atom, pyrrolidino, piperidino, hexamethyleneimino, morpholino, or N'-methylpiperazino, where each of the heterocycles may have one or two alkyl of 1 to 3 carbon atoms or one or two methoxy substituents attached thereto;
$R_3$,—$R_4$ and $R_5$ are each hydrogen or methyl;
$R_6$—is alkyl of 1 to 4 carbon atoms; and
A—is alkylene of 2 to 4 carbon atoms;
and non-toxic, pharmacologically acceptable acid addition salts thereof.

Examples of specific embodiments of the alkyl variants of $R_1$ and $R_2$ are the following: Methyl, ethyl, n-propyl, isopropyl, n-butyl, isobutyl, sec. butyl, tert. butyl, amyl, isoamyl and n-hexyl.

The compounds embraced by formula I may be prepared by the following methods:

Method A

By reacting an alkali metal salt of a pyridobenzodiazepinone of the formula

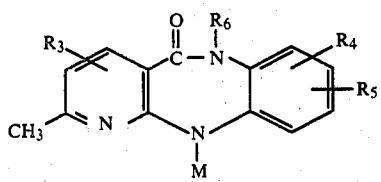

wherein $R_3$, $R_4$, $R_5$ and $R_6$ have the same meanings as in formula I, and
M—is an alkali metal,
with an amine of the formula

wherein
$R_1$,—$R_2$ and A have the same meanings as in formula I, and
X is a reactive ester component of an inorganic or strong organic acid, such as halogen or tosyl.

The reaction is carried out in the presence of an inert solvent, such as xylene, toluene, dioxane, dimethylformamide or acetone, at a temperature between 20° and 250° C.

The alkali metal salt of the formula II is preferably formed in situ in the reaction mixture only a short time before performance of the reaction, for example by the action of sodium hydroxide, potassium hydroxide, lithium hydroxide, sodium hydride, potassium hydride, lithium hydride or sodium amide upon the corresponding free pyridobenzodiazepinone, that is, the corresponding compound of the formula II where M is hydrogen.

Method B

By reacting a pyridobenzodiazepinone of the formula

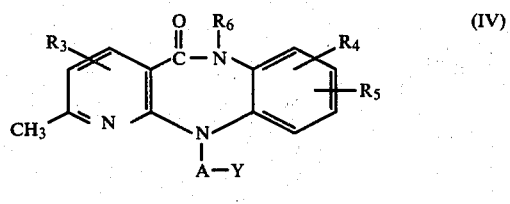

wherein
$R_3$,—$R_4$, $R_5$, $R_6$ and A have the same meanings as in formula I, and
Y—is halogen, preferably chlorine, or tosyl,
with an amine of the formula

wherein
$R_1$ and $R_2$ have the same meanings as in formula I.

The reaction is carried out in the presence of an inert organic solvent or in an excess of the amine of the formula V at temperatures between −20° and +80° C. Examples of suitable inert solvents are xylene, toluene, dioxane, dimethyl formamide or acetone.

Method C

By thermal decarboxylation of a pyridobenzodiazepinone of the formula

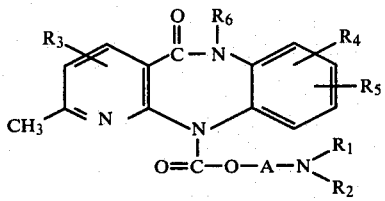

wherein

R$_1$, R$_2$, R$_3$, R$_4$, R$_5$, R$_6$ and A have the same meanings as in formula I.

The decarboxylation is carried out at temperatures between 150° C. and 250° C., optionally in the presence of an inert solvent, such as diethylene glycol, sulfolane, o-dichlorobenzene or tetraethylene glycol dimethyl ether.

If the end product of method A, B or C is a compound of the formula I wherein R$_1$ is benzyl, the same may be converted into the corresponding compound of the formula I wherein R$_1$ is hydrogen by hydrogenolytic removal of the benzyl group. The hydrogenolysis is effected with catalytically activated hydrogen at a temperature between 20° and 100° C. and a hydrogen pressure between 1 and 100 atmospheres. Especially suitable catalysts are noble metal catalysts, such as palladium-on-charcoal.

The pyridobenzodiazepinone starting compounds of the formula II wherein M is initially hydrogen may be obtained by reacting a 2-halo-nicotinic acid of the formula

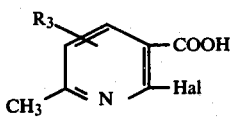

wherein

R$_1$—has the same meanings as in formula I, and
Hal—is halogen, with an o-phenylenediamine of the formula

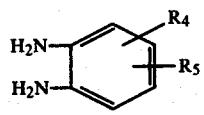

wherein

R$_4$ and R$_5$ have the same meanings as in formula I, at temperatures above 150° C., optionally in the presence of an inert, high-boiling-point solvent such as tetrahydronaphthalene, dichloro- or trichloro-benzene or glycol, butyl glycol or sulfolane and of an inert gas, whereby first the 6,11-dihydro-5H-pyrido[2,3-b][1,5]benzodiazepine-5-one of the formula

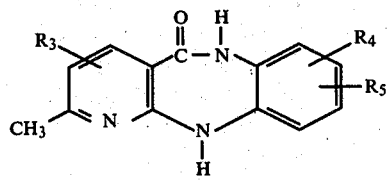

is obtained, which is subsequently converted to the corresponding pyridobenzodiazepinone of the formula II wherein M is hydrogen by heating it with an alkyl iodide in ethanol in the presence of sodium hydroxide or with an alkyl iodide in dimethyl formamide and sodium hydride in mineral oil to reflux temperature (see German Pat. Nos. 1,238,479 and 1,251,767).

The starting compounds of the formula VII are obtained by hydrolysis of a corresponding 2-halo-3-cyano-pyridine (prepared, for example, according to the method of Jahine, J. prakt. Chemie 316, 337 [1974]) by means of concentrated mineral acids, such as sulfuric acid and nitric acid.

The pyridobenzodiazepinones of the formula IV may be obtained by reacting a corresponding pyridobenzodiazepinone of the formula II in the form of an alkali metal salt, i.e. for example in the presence of sodium hydride or sodium hydrazide, with a dihalo-alkane such as 1-bromo-3-chloro-propane, preferably in the presence of an inert solvent at room temperature.

The starting compounds of the formulas III and V are described in the literature or may be prepared by methods described in the literature.

The starting compounds of the formula VI may be prepared by reacting a pyridobenzodiazepinone of the formula

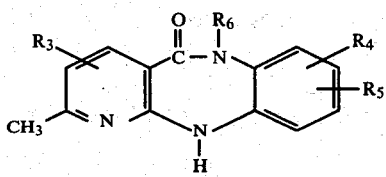

wherein R$_3$, R$_4$, R$_5$ and R$_6$ have the same meanings as in formula I, with phosgene in toluene or diethylketone in the presence of pyridine at temperatures between 50° and 110° C., and subsequently reacting the carboxylic acid chloride intermediate formed thereby with an aminoalcohol of the formula

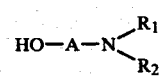

wherein R$_1$, R$_2$ and A have the same meanings as in formula I, in an inert organic solvent at temperatures between 100° and 150° C.

The compounds embraced by formula I are organic bases and therefore form acid additiion salts with inorganic or organic acids. Examples of non-toxic, pharmacologically acceptable acid addition salts are those formed with hydrochloric acid, hydrobromic acid, sulfuric acid, phosphoric acid, maleic acid, fumaric acid, citric acid, tartaric acid, malic acid, 8-chlorotheophylline or the like.

The following examples illustrate the present invention and will enable others skilled in the art to understand it more completely. It should be understood, however, that the invention is not limited solely to the particular examples given below.

PREPARATION OF STARTING COMPOUNDS

EXAMPLE A 6,11-Dihydro-2,6-dimethyl-5H-pyrido[2,3-b][1,5]benzodiazepin-5-one

A mixture consisting of 11.3 gm (0.05 mol) of 6,11-dihydro-2-methyl-5H-pyrido[2,3-b][1,5]-benzodiazepin- 5-one (prepared according to C.A. 74, 53868y, 1971), 150 ml of dimethyl formamide, and 2.8 gm of 50% sodium hydride in mineral oil was stirred at 30° C. in a nitrogen atmosphere for 1 hour. Then, a solution of 10.7 gm (0.075 mol) of methyl iodide in 30 ml of dimethyl formamide was added dropwise while stirring, and the mixture was heated on an oil bath at 100° C. for 3 hours while stirring and then evaporated in vacuo, and an aqueous sodium carbonate solution was stirred into the residue. The mixture was suction-filtered, and the filter cake was washed with water and recrystallized from xylene, yielding 80% of theory of the compound named in the heading, which had a melting point of 192°–194° C.

Elemental analysis: $C_{14}H_{13}N_3O$; mol. wt. 239.3; Calculated: C-70.28%; H-5.47%; N-17.56%; Found: C-70.10%; H-5.50%; N-17.62%.

EXAMPLE B 6,11-Dihydro-2,6,8,9-tetramethyl-5H-pyrido[2,3-b][1,5]benzodiazepin-5-one A mixture consisting of 38 gm (0.15 mol) of 6,11-dihydro-2,8,9-trimethyl-5H-pyrido[2,3-b][1,5]benzodiazepin-5-one, 300 ml of dimethyl formamide and 8.4 gm (0.18 mol) of 50% sodium hydride in mineral oil was stirred at room temperature in a nitrogen atmosphere for 30 minutes. Then, a solution of 31.4 gm (0.22 mol) of methyl iodide in 50 ml of dimethyl formamide was added dropwise, and the mixture was heated on an oil bath at 100° C. for 2 hours while stirring. The mixture was then evaporated in vacuo, ice was added to the oily residue, and the mixture was stirred until the residue crystallized. The crystals were collected by suction filtration and recrystallized from n-propanol, yielding 65% of theory of the compound named in the heading, which had a melting point of 217°–219° C.

Elemental analysis: $C_{16}H_{17}N_3O$; mol. wt. 267.3; Calculated: C-71.89%; H-6.41%; N-15.72%; Found: C-72.05%; H-6.57%; N-15.94%.

EXAMPLE C

2-Chloro-4,6-dimethyl-nicotinic acid

A mixture consisting of 15 gm of 2-chloro-3-cyano-4,6-dimethyl-pyridine [see Jahine, J. prakt. Chem. 316,337 (1974)], 40 ml of concentrated sulfuric acid and 13 ml of fuming nitric acid was heated while stirring. At 95° C. an exothermic reaction took place. By cooling with ice water the temperature was maintained at 95°–100° C. After the exothermic reaction had subsided, the mixture was stirred for 30 minutes more at 100° C. and then poured on ice and adjusted to a pH-value of 3–4 with ammonia. The resulting precipitate was collected by suction filtration, washed with water, dehydrated by boiling with toluene in a vessel equipped with a water trap, and recrystallized from toluene, yielding 80% of theory of the compound named in the heading, which had a melting point of 159°–160° C.

Elemental analysis: $C_8H_8ClNO_2$; mol. wt. 185.6; Calculated: C-51.77% H-4.34%; Cl-19.10%; N-7.55%; Found: C-51.85% H-4.36%; Cl-19.25%; N-7.56%.

EXAMPLE D 6,11-Dihydro-2,4-dimethyl-5H-pyrido[2,3-b][1,5]benzodiazepin-5-one

A mixture consisting of 9.3 gm of 2-chloro-4,6-dimethyl-nicotinic acid, 5.41 gm of o-phenylenediamine and 25 ml of butyl glycol was heated at 170° C. for 90 minutes while stirring. The mixture was subsequently cooled to 60° C. and poured over ice. After adjusting it to a pH-value of 8 with ammonia, the mixture was suction-filtered, and the filter cake was washed with water and recrystallized from aqueous 70% acetic acid, yielding 53% of theory of the compound named in the heading, which had a melting point of 297°–299° C.

Elemental analysis: $C_{14}H_{13}N_3O$; mol. wt. 239.3; Calculated: C-70.28%; H-5.47%; N-17.56% Found: C-70.50%; H-5.55%; N-17.75%.

EXAMPLE E 6,11-Dihydro-2,4,6-trimethyl-5H-pyrido[2,3b][1,5]benzodiazepin-5-one A mixture consisting of 24 gm of 6,11-dihydro-2,4-dimethyl-5H-pyrido[2,3-b][1,5]benzodiazepin-5-one, 300 ml of dimethyl formamide and 5.7 gm of 50% sodium hydride in mineral oil was stirred in a nitrogen atmosphere for one hour. Then, a solution of 21.3 gm of methyl iodide in 50 ml of dimethyl formamide was added dropwise and the mixture was stirred on an oil bath at 100° C. for 3 hours, then evaporated in vacuo, and the residue was stirred with water. The aqueous mixture was suction-filtered, the 2,4,6,11-tetramethyl derivative which had formed simultaneously was separated by passing the filter cake through a silica gel column, and the desired product was recrystallized from xylene, yielding 36% of theory of the compound named in the heading, which had a melting point of 272°–273° C.

Elemental analysis: $C_{15}H_{15}N_3O$; mol. wt. 253.3; Calculated: C-71.13%; H-5.97%; N16.59%; Found: C-71.40%; H-6.06%; N-16.73%.

EXAMPLE F 11-(3-Chloro-propyl)-6,11-dihydro-2,4,6-trimethyl-5H-pyrido-[2,3-b][1,5]benzodiazepin-5-one 2.47 gm of 6,11-dihydro-2,4,6-trimethyl-5H-pyrido-[2,3-b][1,5]benzodiazepin-5-one were dissolved in 15 ml of dimethyl formamide, 0.76 gm of 50% sodium hydride in mineral oil was added, and the mixture was stirred at room temperature for one hour. Then, 1.7 ml of 1-bromo-3-chloro-propane were added, and the mixture was stirred at room temperature for 5 hours. After standing overnight, 100 ml of methylene chloride were added and the reaction mixture was washed three times with water. The organic phase was dried over sodium sulfate and evaporated in vacuo at room temperature. The crystalline residue was digested with a mixture of 7 ml of chloroform and 7 ml of ethyl acetate, and the mixture was suction-filtered. The filter cake was recrystallized from absolute ethanol, yielding 52% of theory of 11-(3-chloro-propyl)-6,11-dihydro-2,4,6-trimethyl-5H-pyrido[2,3-b][1,5]benzodiazepin-5-one having a melting point of 161°–163° C.

Elemental analysis: $C_{18}H_{20}ClN_3O$; mol. wt. 329.8; Calculated: C-65.54%; H-6.11%; Found: C-66.0%; H-6.19%.

EXAMPLE G

3-Diethylamino-propyl 6,11-dihydro-2,4,6-trimethyl-5H-pyrido-[2,3-b][1,5]benzodiazepin-5-one-11-carboxylate (a) 50 ml of a 20% solution of phosgene in toluene were added dropwise over a period of 10 minutes to a mixture consisting of 10.0 gm of 6,11-dihydro-2,4,6- trimethyl-5H-pyrido[2,3-b][1,5]-benzodiazepin-5-one, 100 ml of diethyl ketone, 50 ml of toluene and 5 ml of pyridine. The resulting mixture was heated at 60° C. for 2 hours, at 80° C. for one hour and at 110° C. for one hour, while stirring. After cooling to room temperature, 100 ml of water were added. The organic phase was dried with sodium sulfate and then evaporated in vacuo. The residue was recrystallized twice from ethanol, yielding 7.3 gm of 11-chloroformyl-6,11-dihydro-2,4,6-trimethyl-5H-pyrido[2,3-b][1,5]benzodiazepin-5-one, m.p. 205°–207° C.

Elemental analysis: $C_{16}H_{14}ClN_3O_2$; mol. wt. 315.76; Calculated: C-60.86%; H-4.46%; N-13.30%; Cl-11.22%; Found: C-61.00%; H-4.53%; N-13.35%; Cl-11.13%.

(b) 5.0 gm of the chloroformyl compound obtained in step (a) were boiled with 4.2 gm of 3-diethylaminopropanol-1 in 50 ml of chlorobenzene for 4 hours. The cooled reaction solution was then admixed with 100 ml of aqueous 20% acetic acid, and the acidic phase was separated and made alkaline with sodium carbonate. The precipitate formed thereby was taken up in ether, and the ethereal solution was dried with sodium sulfate and evaporated. The residue was recrystallized from cyclohexane, yielding 4.1 gm of (3-diethylamino-propyl) 6,11-dihydro-2,4,6-trimethyl-5H-pyrido[2,3-b]-[1,5]benzodiazepin-5-one-11-carboxylate, m.p. 93°–94° C.

Elemental analysis: $C_{23}H_{30}N_4O_3$; mol. wt. 410.5; Calculated: C-67.29%; H-7.37%; N-13.65%; Found: C-67.50%; H-7.51%; N-13.45%.

EXAMPLE H 6,11-Dihydro-2,4,8(or 9)-trimethyl-5H-pyrido[2,3-b][1,5]benzodiazepin-5-one A mixture consisting of 93 gm of 2-chloro-4,6-dimethyl-nicotinic acid, 61 gm of 3,4-diamino-toluene and 60 ml of sulfolane was heated on an oil bath, while stirring. After heating the mixture at 200° to 210° C. for 20 minutes, it was cooled to 100° C., and the contents of the flask were poured over ice while stirring. The crude product precipitated thereby was admixed with 500 ml of aqueous 20% acetic acid, and the insoluble matter was suction-filtered off, recrystallized from aqueous 90% acetic acid in the presence of charcoal, and again recrystallized from 90% dimethyl formamide, yielding 32% of theory of the compound named in the heading, which had a melting point of 272°–276° C.

Elemental analysis: $C_{15}H_{15}N_3O$; mol. wt. 253.3; Calculated: C-71.13%; H-5.97%; N-16.59%; Found: C-71.00%; H-5.89%; N-16.75%.

EXAMPLE I 6,11-Dihydro-2,4,6,8(or 9)-tetramethyl-5H-pyrido[2,3-b][1,5]-benzodiazepin-5-one A mixture consisting of 12.7 gm of 6,11-dihydro-2,4,8(or 9)-trimethyl-5H-pyrido[2,3-b][1,5]benzodiazepin-5-one, 130 ml of dimethyl formamide and 2.4 gm of 50% sodium hydride in mineral oil was stirred on an oil bath at 60° C. for 30 minutes in a nitrogen atmosphere. Then, a solution of 8.5 gm of methyl iodide in 30 ml of dimethyl formamide was added dropwise. The resulting mixture was stirred on an oil bath at 120° C. for one hour and was then evaporated in vacuo. The residue was admixed with water, the mixture was made alkaline with ammonia and was then extracted repeatedly with chloroform. The combined chloroform extracts were dried with sodium sulfate. After distilling off the chloroform, the residue was recrystallized from a mixture of petroleum ether (b.p. 100°–140° C.) and xylene (1:1), yielding 65% of theory of the compound named in the heading, which had a melting point of 200°–204° C.

Elemental analysis: $C_{16}H_{17}N_3O$; mol. wt. 267.3; Calculated: C-71.89%; H-6.41%; N-15.72%; Found: C-71.90%; H-6.42%; N-15.85%.

EXAMPLE J 6,11-Dihydro-2,4,8,9-tetramethyl-5H-pyrido[2,3-b][1,5]benzodiazepin-5-one A mixture consisting of 52.0 gm of 2-chloro-4,6-dimethyl-nicotinic acid, 38.0 gm of 4,5-dimethyl-o-phenylenediamine and 150 ml of sulfolane was heated on an oil bath at 220° C. After 45 minutes the mixture was allowed to cool to 100° C. and was then poured over ice. After neutralization with ammonia and standing for several hours the precipitate which had formed was suction-filtered off and admixed with dilute acetic acid. The mixture was suction-filtered after one hour, and the filter cake was recrystallized from aqueous 80% acetic acid, yielding 34% of theory of the compound named in the heading, which had a melting point of 264°–268° C.

Elemental analysis: $C_{16}H_{17}N_3O$; mol. wt. 267.3; Calculated: C-71.89%; H-6.41%; N-15.72%; Found: C-72.00%; H-6.52%; N-15.80%.

EXAMPLE K 6,11-Dihydro-2,4,6,8,9-pentamethyl-5H-pyrido[2,3-b][1,5]benzodiazepin-5-one A mixture consisting of 6.7 gm of 6,11-dihydro-2,4,8,9-tetramethyl-5H-pyrido[2,3-b][1,5]benzodiazepin-5-one, 150 ml of dimethyl formamide and 1.4 gm of 50% sodium hydride in mineral oil was stirred at 50° C. in a nitrogen atmosphere for 30 minutes. Thereafter, a solution of 7.1 gm of methyl iodide in 30 ml of dimethyl formamide was added dropwise at room temperature. The resulting mixture was heated on an oil bath at 120° C. for 1 hour, and was then evaporated in vacuo. The residue was admixed with water, the aqueous mixture was made alkaline with ammonia, and it was then extracted with chloroform. After separation of the 2,4,6,8,9,11-hexamethyl compound which had simultaneously formed in a silica gel column, the product was recrystallized from petroleum ether (b.p. 100°–140° C.), yielding 63% of theory of the compound named in the heading, which had a melting point of 225°–227° C.

Elemental analysis: $C_{17}H_{19}N_3O$; mol. wt. 281.4; Calculated: C-72.57%; H-6.81%; N-14.93%; Found: C-72.50%; H-6.80%; N-15.00%.

Preparation of end products of the formula I

Whenever the following examples refer to the purification of a product by means of a silica gel column, the eluant which was used was a mixture of chloroform, methanol, cyclohexane and concentrated ammonia in the volumetric ratio of 68:15:15:2, unless otherwise specified.

EXAMPLE 1

11-(2-Diethylamino-ethyl)-6,11-dihydro-2,6-dimethyl-5H-pyrido-[2,3-b][1,5]benzodiazepin-5-one by method A A mixture consisting of 7.2 gm of 6,11-dihydro-2,6-dimethyl-5H-pyrido[2,3-b][1,5]benzodiazepin-5-one, 70 ml of dimethyl formamide and 1.9 gm of 50% sodium hydride in mineral oil was stirred at 30° to 50° C. in a nitrogen atmosphere for 30 minutes. Thereafter, a solution of 6.8 gm of 2-diethylaminoethyl chloride in 30 ml of dimethyl formamide was added dropwise, and the mixture was stirred at 100° C. for 2 hours and then evaporated in vacuo. The residue was admixed with an aqueous potassium carbonate solution, and the mixture was extracted with ether. The evaporation residue of the combined ether extracts, which were dried with sodium sulfate, was purified in a silica gel column and recrystallized from petroleum ether (b.p. 100°–140° C.), yielding 62% of theory of the compound of the formula

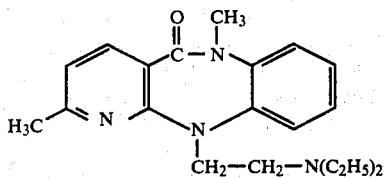

which had a melting point of 91°–93° C.

Elemental analysis: $C_{20}H_{26}N_4O$; mol. wt. 338.5; Calculated: C-70.98%; H-7.74%; N-16.55%; Found: C-71.05%; H-7.73%; N-16.30%.

EXAMPLE 2

6,11-Dihydro-2,6-dimethyl-11-(3-dimethylamino-propyl)-5H-pyrido[2,3-b][1,5]benzodiazepin-5-one by method A A mixture consisting of 7.2 gm of 6,11-dihydro-2,6-dimethyl-5H-pyrido[2,3-b][1,5]benzodiazepin-5-one, 70 ml of dimethyl formamide and 1.9 gm of 50% sodium hydride in mineral oil was stirred at 30°–50° C. in a nitrogen atmosphere for 30 minutes. Then, a solution of 6.1 gm of 3-diethylamino-propyl chloride in 30 ml of dimethyl formamide was added dropwise, and the mixture was heated on an oil bath at 120° C. for 3 hours and then evaporated in vacuo. The residue was mixed with an aqueous potassium carbonate solution, and the mixture was extracted with ether. The ethereal phase was dried with sodium sulfate and evaporated, and the residue was recrystallized from petroleum ether (b.p. 100°–140° C.), yielding 76% of theory of the compound named in the heading, which had a melting point of 130°–131° C.

Elemental analysis: $C_{19}H_{24}N_4O$; mol. wt. 324.4; Calculated: C-70.34%; H-7.46%; N-17.27%; Found: C-70.35%; H-7.45%; N-17.34%.

EXAMPLE 3

11-(3-Diethylamino-propyl)-6,11-dihydro-2,6-dimethyl-5H-pyrido[2,3-b][1,5]benzodiazepin-5-one by method A A mixture consisting of 6.8 gm of 6,11-dihydro-2,6-dimethyl-5H-pyrido[2,3-b][1,5]benzodiazepin-5-one, 100 ml of dimethyl formamide and 1.9 gm of 50% sodium hydride in mineral oil was stirred at 30°–50° C. in a nitrogen atmosphere for 45 minutes. Thereafter, a solution of 7.5 gm of 3-diethylamino-propyl chloride in 35 ml of dimethyl formamide was added dropwise at 25° C., and the mixture was stirred on an oil bath at 120° C. for 2 hours. The resulting solution was evaporated in vacuo, the residue was admixed with dilute ammonia, and the mixture was extracted with ether. The organic phase was dried over sodium sulfate and then evaporated, and the residue was recrystallized from petroleum ether, yielding 81% of theory of the compound named in the heading, which had a melting point of 76°–78° C.

Elemental analysis: $C_{21}H_{28}N_4O$; mol. wt. 325.5; Calculated: C-71.56%; H-8.01%; N-15.89%; Found: C-71.40%; H-8.10%; N-15.97%.

The same yield of the same compound was obtained when potassium hydride or lithium hydride was used in the process instead of sodium hydride.

The hydrochloride, m.p. 274°–275° C. (decomp.), was obtained by dissolving the free base in acetonitrile, acidifying the solution with hydrochloric acid, and recrystallizing the precipitate formed thereby from ethanol.

Elemental analysis of hydrochloride: $C_{21}H_{29}ClN_4O$; mol. wt. 388.9; Calculated: C-64.85%; H-7.51%; N-14.40%; Cl-9.11%; Found: C-64.60%; H-7.77%; N-14.18%; Cl-9.12%.

EXAMPLE 4

11-[3-(N-Ethyl-N-isopropyl-amino)-propyl]-6,11-dihydro-2,6-dimethyl-5H-pyrido[2,3-b][1,5]benzodiazepin-5-one by method A A mixture consisting of 4.5 gm of 6,11-dihydro-2,6-dimethyl-5H-pyrido-[2,3-b][1,5]benzodiazepin-5-one, 60 ml of dioxane and 1.27 gm of 50% sodium hydride in mineral oil was stirred at 90° C. for 1 hour. Thereafter, 4.3 gm of 3-(N-ethyl-N-isopropyl-amino)-propyl chloride were added dropwise, and the mixture was refluxed for 17 hours. The reaction solution was then evaporated in vacuo, and the residue was purified over a silica gel column and recrystallized from petroleum ether, yielding 36% of theory of the compound named in the heading, which had a melting point of 104°–105° C.

Elemental analysis: $C_{22}H_{30}N_4O$; mol. wt. 366.5; Calculated: C-72.10%; H-8.25%; N-15.29%; Found: C-71.80%; H-8.42%; N-15.50%.

EXAMPLE 5

6,11-Dihydro-11-(3-diisopropylamino-propyl)-2,6-dimethyl-5H-pyrido[2,3-b][1,5]benzodiazepin-5-one by method A A mixture consisting of 4.5 gm of 6,11-dihyrdo-2,6-dimethyl-5H-pyrido[2,3-b][1,5]benzodiazepin-5-one, 60 ml of dimethyl formamide and 1.27 gm of 50% sodium hydride in mineral oil was stirred at 90° C. for 1 hour. Thereafter, 4.6 gm of 3-diisopropylamino-propyl chloride were added dropwise and the mixture was stirred at 120° C. for 2 hours. The reaction solution was then evaporated in vacuo, and the residue was dissolved in a mixture of ether and dilute ammonia. The organic phase was separated, dried over sodium sulfate and evaporated. The oily residue was distilled, and the fraction passing over between 189°–193° C. at 0.13 mm Hg was recrystallized from petroleum ether, yielding 31% of theory of the compound named in the heading, which had a melting point of 118°–119° C.

Elemental analysis: $C_{23}H_{32}N_4O$; mol. wt. 380.5; Calculated: C-72.60%; H-8.48%; N-14.72%; Found: C-72.90%; H-8.51%; N-14.80%.

EXAMPLE 6

6,11-Dihydro-2,6-dimethyl-11-(3-pyrrolidino-propyl)-5H-pyrido[2,3-b][1,5]benzodiazepin5-one by method A A mixture consisting of 7.2 gm of 6,11-dihydro-2,6-dimethyl-5H-pyrido[2,3-b][1,5]benzodiazepin-5-one, 1.9 gm of 50% sodium hydride in mineral oil and 100 ml of dimethyl formamide was stirred at 60°–70° C. for 45 minutes. Thereafter, the mixture was cooled to room temperature, 7.4 gm of 3-pyrrolidino-propyl chloride were added dropwise and the mixture was refluxed for 3 hours. The solvent was then distilled off in vacuo, and the residue was recrystallized twice from acetonitrile, yielding 46% of theory of the compound named in the heading, which had a melting point of 134°–136° C.

Elemental analysis $C_{20}H_{26}N_4O$; mol. wt. 350–5; Calculated: C-71.97%; H-7.48%; N-15.99%; Found: C-72.00%; H-7.54%; N-15.68%.

EXAMPLE 7

6,11-Dihydro-2,6-dimethyl-11-(3-piperidino-propyl)-5H-pyrido-[2,3-b][1,5]benzodiazepin-5-one by method A A mixture consisting of 7.2 gm of 6,11-dihydro-2,6-dimethyl-5H-pyrido[2,3-b][1,5]benzodiazepin-5-one, 1.9 gm of 50% sodium hydride in mineral oil and 100 ml of dimethyl formamide was stirred at 60°–70° C. for 1 hour. Thereafer, 8.1 gm of 3-piperidino-propyl chloride were added dropwise at room temperature, and the mixture was refluxed for 5 hours. After distilling off the solvent in vacuo, the residue was recrystallized from acetonitrile, yielding 54% of theory of the compound named in the heading, which had a melting point of 145°–146° C.

The hydrochloride, m.p. 260°–261° C. (decomp.), was obtained by dissolving the free base in ethyl acetate, acidifying the solution with ethereal hydrochloric acid, and recrystallizing the salt from acetonitrile.

Elemental analysis of hydrochloride: $C_{22}H_{29}ClN_4O$; mol. wt. 400.96; Calculated: C-65.90%; H-7.29%; N-13.97%; Cl-8.84%; Found: C-65.70%; H-7.25%; N-13.95%; Cl-8.85%.

EXAMPLE 8

6,11-Dihydro-2,6-dimethyl-11-(3-hexamethyleneimino-propyl)-5H-pyrido[2,3-b][1,5]benzodiazepin-5-one by method A A mixture consisting of 7.2 gm of 6,11-dihydro-2,6-dimethyl-5H-pyrido[2,3-b][1,5]benzodiazepin-5-one, 1.9 gm of 50% sodium hydride in mineral oil and 100 ml of dimethyl formamide was stirred at 60°–70° C. for one hour. Thereafter, 8.7 gm of 3-hexamethyleneimino-propyl chloride were added dropwise at room temperature, and the mixture was refluxed for 5 hours. After distilling off the solvent in vacuo, the residue was recrystallized three times from cyclohexane, yielding 48% of theory of the compound named in the heading, which had a melting point of 114°–115° C.

Elemental analysis: $C_{23}H_{30}N_4O$; mol. wt. 387.5; Calculated: C-72.98%; H-7.99%; N-14.80%; Found: C-73.30%; H-7.88%; N-14.90%.

EXAMPLE 9

11-(3-Diethylamino-propyl)-6,11-dihydro-2,6,8,9-tetramethyl-5H-pyrido[2,3-b][1,5]benzodiazepin-5-one hydrogen fumarate by method A A mixture consisting of 8.0 gm of 6,11-dihydro-2,6,8,9-tetramethyl-5H-pyrido[2,3-b][1,5]benzodiazepin-5-one, 100 ml of dimethyl formamide and 1.9 gm of 50% sodium hydride in mineral oil was stirred in a nitrogen atmosphere at room temperature for 30 minutes. Thereafter, a solution of 7.5 gm of 3-diethylamino-propyl chloride in 35 ml of dimethyl formamide was added dropwise, and the mixture was stirred on an oil bath at 120° C. for 2 hours. The reaction solution was then evaporated in vacuo, the residue was dissolved in dilute hydrochloric acid, and the solution was heated with charcoal and filtered. The filtrate was made alkaline with potassium carbonate and then extracted with ether. The evaporation residue of the ether extract was dissolved in isopropanol, and fumaric acid was added to the solution until it reacted weakly acid. The precipitate formed thereby was recrystallized from isopropanol, yielding 75% of theory of the compound named in the heading, which had a melting point of 167°–169° C.

Elemental analysis: $C_{27}H_{36}N_4O_5$; mol. wt. 496.6; Calculated: C-65.30%; H-7.31%; N-11.28%; Found: C-65.20%; H-7.26%; N-11.45%.

EXAMPLE 10

11-(3-Diethylamino-propyl)-6,11-dihydro-2,4,6-trimethyl-5H-pyrido[2,3-b][1,5]benzodiazepin-5-one by method A A mixture consisting of 9.9 gm of 6,11-dihydro-2,4,6-trimethyl-5H-pyrido[2,3-b][1,5]benzodiazepin-5-one, 100 ml of dimethyl formamide and 2.4 gm of 50% sodium hydride in mineral oil was stirred in a nitrogen atmosphere at 50°–60° C. for 1 hour. After cooling to room temperature, a solution of 7.5 gm of 3-diethylamino-propyl chloride in 35 ml of dimethyl formamide was added dropwise and the mixture was heated on an oil bath at 120° C. for 3 hours. Thereafter, the mixture was evaporated in vacuo, and the residue was admixed with an aqueous potassium carbonate solution and extracted with chloroform. After drying the extract solution with sodium sulfate, the chloroform was distilled off, and the residue was recrystallized from acetonitrile, yielding 76% of theory of the compound named in the heading, which had a melting point of 149°–151° C.

Elemental analysis: $C_{22}H_{30}N_4O$; mol. wt. 366.5; Calculated: C-72.10%; H-8.25%; N-15.29%; Found: C-72.20%; H-8.30%; N-15.31%.

The hydrochloride, prepared from the free base with ethereal hydrochloric acid in isopropanol, had a melting point of 281°–283° C. (decomp.)

Elemental analysis of hydrochloride: $C_{22}H_{31}ClN_4O$; mol. wt. 403.0; Calculated: C-65.57%; H-7.75%; N-13.90%; Cl-8.80%; Found: C-65.30%; H-7.63%; N-14.08%; Cl-8.83%.

EXAMPLE 11

11-(3-Ethylamino-propyl)-6,11-dihydro-2,4,6-trimethyl-5H-pyrido[2,3-b][1,5]benzodiazepin-5-one (a) A mixture consisting of 12.3 gm of 6,11-dihydro-2,4,6-trimethyl-5H-pyrido[2,3-b][1,5]benzodiazepin-5-one, 120 ml of dimethyl formamide and 3.05 gm of 50% sodium hydride in mineral oil was stirred at 60° C. for 2 hours. Thereafter, 17 gm of 3-(N-ethyl-N-benzyl-amino)-propyl chloride were added dropwise, and the solution was stirred at 120° C. for 2 hours. After evaporating the solution in vacuo, the residue was distilled, yielding 68% of theory of 11-[3-(N-ethyl-N-benzyl-amino)-propyl]-6,11-dihydro-2,4,6-trimethyl-5H-pyrido[2,3-b][1,5]benzodiazepin-5-one having a b.p. of 236°–238° C. at 0.3 mm Hg.

Elemental analysis: $C_{27}H_{32}N_4O$; mol. wt. 428.6; Calculated: C-75.66%; H-7.52%; Found: C-75.90%; H-7.79%.

(b) 14 gm of the end product of step (a) were hydrogenated in 400 ml of methanol in the presence of 5 gm of 10% palladium-on-charcoal at 50° C. and 50 atmospheres. After separating the catalyst, the reaction mixture was evaporated in vacuo, and the residue was purified on a silica gel column. Then, the product was recrystallized from petroleum ether (b.p. 100°–140° C.), yielding 42% of theory of 11-(3-ethylamino-propyl)-6,11-dihydro-2,4,6-trimethyl-5H-pyrido[2,3-b][1,5]benzodiazepin-5-one which had a m.p. of 101°–103° C.

Elemental analysis: $C_{20}H_{26}N_4O$; mol. wt. 338.5; Calculated: C-70.98%; H-7.74%; N-16.55%; Found: C-70.60%; H-7.65%; N-16.80%.

EXAMPLE 12

6,11-Dihydro-11-(2-morpholino-ethyl)-2,4,6-trimethyl-5H-pyrido[2,3-b][1,5]benzodiazepin-5-one by method A A mixture consisting of 5.06 gm of 6,11-dihydro-2,4,6-trimethyl-5H-pyrido[2,3-b][1,5]benzodiazepin-5-one, 1.1 gm of 50% sodium hydride in mineral oil and 60 ml of dimethyl formamide was stirred at 80° C. for 1 hour. Then, 4.5 gm of 2-morpholino-ethyl chloride were added, and the mixture was stirred at 120° C. for 3.5 hours more. The precipitate formed thereby was suction-filtered off, the solvent was removed from the filtrate in vacuo, and the oily residue was purified on a silica gel column. The product was recrystallized from petroleum ether (b.p. 100°–140° C.), yielding 64% of theory of the compound named in the heading, which had a melting point of 133°–135° C.

Elemental analysis: $C_{21}H_{26}N_4O_2$; mol. wt. 366.5; Calculated: C-68.83%; H-7.15%; N-15.29%; Found: C-68.80%: H-7.23%; N-15.35%.

EXAMPLE 13

6,11-Dihydro-11-[3-(N'-methyl-piperazino)-propyl]-2,4,6-trimethyl-5H-pyrido[2,3-b][1,5]benzodiazepin-5-one by method A A mixture consisting of 5.06 gm of 6,11-dihydro-2,4,6-trimethyl-5H-pyrido[2,3-b][1,5]benzodiazepin-5-one, 1.1 gm of 50% sodium hydride in mineral oil and 60 ml of dimethyl formamide was stirred at 80° C. for 1 hour. Thereafter, 5.28 gm of 3-(N'-methyl-piperazino)-propyl chloride were added, and the mixture was stirred at 120° C. for 1.5 hours, then suction-filtered, and the solvent was distilled out of the filtrate in vacuo. The residue was stirred with ether, and the crystals formed thereby were suction-filtered off and recrystallized from acetonitrile in the presence of charcoal, yielding 62% of theory of the compound named in the heading, which had a melting point of 157°–159° C.

Elemental analysis: $C_{23}H_{31}N_5O$; mol. wt. 393.5; Calculated: C-70.20%; H-7.94%; N-17.80%; Found: C-70.20%; H-7.84%; N-18.05%.

EXAMPLE 14

11-(3-Diethylamino-propyl)-6,11-dihydro-2,4,6,8(or 9)-tetramethyl-5H-pyrido[2,3-b][1,5]benzodiazepin-5-one by method A A mixture consisting of 7.5 gm of 6,11-dihydro-2,4,6,8(or 9)-tetramethyl-5H-pyrido[2,3-b][1,5-benzodiazepin-5-one, 100 ml of dimethyl formamide and 1.44 gm of 50% sodium hydride in mineral oil was stirred at 40° C. in a nitrogen atmosphere for 30 minutes. Then, a solution of 7.5 gm of 3-diethylamino-propyl chloride in 35 ml of dimethyl formamide was added dropwise. After heating the mixture on an oil bath at 100° C. for 1 hour, it was evaporated in vacuo, the residue was admixed with an aqueous potassium carbonate solution, and the mixture was extracted with ether. The ether phase was dried with sodium sulfate and evaporated, and the residue was distilled, yielding 63% of theory of the compound named in the heading, which had a b.p. of 186°–190° C. at 0.1 mm Hg.

Elemental analysis: $C_{23}H_{32}N_4O$; mol. wt. 380.5; Calculated: C-72.60%; H-8.48%; N-14.72%; Found: C-72.30%; H-8.35%; N-14.80%.

The dihydrochloride, m.p. 222° C. (decomp.) was prepared by dissolving the free base in acetone and precipitating the salt therefrom with a solution of gaseous hydrogenchloride in dioxane.

Elemental analysis of dihydrochloride: $C_{23}H_{34}Cl_2N_4O$; mol. wt. 453,5; Calculated: C-60.92%; H-7.56%; N-12.36%; Cl-15.64%; Found: C-61.10%; H-7.55%; N-12.60%; Cl-15.38%.

EXAMPLE 15

11-(3-Diethylamino-propyl)-6,11-dihydro-2,4,6,8,9-pentamethyl-5H-pyrido[2,3-b][1,5]benzodiazepin-5-one by method A A mixture consisting of 1.8 mg of 6,11-dihydro-2,4,6,8,9-pentamethyl-5H-pyrido[2,3-b][1,5]benzodiazepin-5-one, 30 ml of dimethyl formamide and 0.34 gm of 50% sodium hydride in mineral oil was stirred in a nitrogen atmosphere at 50° C. for 30 minutes. Then, a solution of 1.5 gm of 3-diethylaminopropyl chloride in 15 ml of dimethyl formamide was added dropwise at room temperature, and the mixture was heated on an oil bath at 120° C. for 2 hours and then evaporated in vacuo. The residue was admixed with dilute ammonia, and the mixture was repeatedly extracted with ether. The combined ether extracts were dried with sodium sulfate, the ether was distilled off, and the residue was recrystallized from petroleum ether (m.p. 100°–140° C.), yielding 53% of theory of the compound named in the heading, which had a melting point of 104°–106° C.

Elemental analysis: $C_{24}H_{34}N_4O$; mol. wt. 394.6; Calculated: C-73.06%; H-8.69%; N-14.20%; Found: C-73.00%; H-8.61%; N-13.97%.

The compounds of the present intention, that is, those embraced by formula I above and their non-toxic, pharmacologically acceptable acid addition salts, have useful pharmacodynamic properties. More particularly, they exhibit very effective bronchosecretolytic activity at very low dosage levels and, in addition, exhibit very good bronchospasmolytic activity in warm-blooded animals, such as guinea pigs. Consequently, the compounds of this invention are eminently useful for the treatment of bronchial asthma.

The bronchosecretolytic activity and the intravenous acute toxicity of the compounds of this invention and of certain related 2-unsubstituted analogs disclosed in German Offenlegungsschrift No. 2,424,811 were ascertained by the standard test methods described below. The table shows the results of these tests for two representative species of the invention and three prior art compounds, where A = 11-(3-Diethylamino-propyl)-6,11-dihydro-2,6-dimethyl-5H-pyrido[2,3-b][1,5]benzodiazepin-5-one hydrochloride, B = 11-(3-Diethylamino-propyl)-6,11-dihydro-2,6,8,9-tetramethyl-5H-pyrido[2,3-b][1,5]benzodiazepin-5-one hydrogen fumarate, X = 11-(3-Diethylamino-propyl)-6,11-dihydro-6-methyl-5H-pyrido[2,3-b][1,5]benzodiazepin-5-one hydrochloride, Y = 11-[3-N-ethyl-N-isopropyl-amino)-propyl]-6,11-dihydro-6-methyl-5H-pyrido[2,3-b][1,5]benzodiazepin-5-one hydrochloride, and Z = 6,11-Dihydro-11-(3-diisopropylamino-propyl)-6-methyl-5H-pyrido[2,3-b][1,5]benzodiazepin-5-one hydrochloride.

The acute toxicity was tested in NMRI-mice of both sexes having a body weight of 20 gm after intravenous administration. 0.1 ml of an aqueous 0.9% sodium chloride solution/10 gm of animal was used as a vehicle. The $LD_{50}$ was calculated according to LITCHFIELD and WILCOXON from the percentage of the animals which died within 14 days after administration of various dosages.

The tests for expectorant activity were carried out according to the method of PERRY, W. and BOYD, E.M.; J. Pharmacol. exp. Therap. 73, 65 (1941), as modified by ENGELHORN, R. and PÜSCHMANN, S.; Arzneimittel Forsch. 21, 1045 (1971), on male guinea pigs with a body weight of 450 to 550 gm, which were anesthetized by i.p.-administration of a * 25% urethane solution (1,0 g/kg). The substances were administered perorally at the indicated dosages levels, each in 2 ml of distilled water, by means of an esophageal tube. 5 tests were carried out per dosage. The increase in bronchial secretion was calculated from the amount secreted within a two-hour period after administration of the test compound in comparison with the values obtained from untreated control animals, also within a two-hour period.

Table

| Compound | Dosage μ g/kg per os | Average percentage change in amount of bronchial secretion in guinea pigs | $LD_{50}$ in the mouse after intravenous administration | |
|---|---|---|---|---|
| | | | mg/kg | Confidence limits (95% probability) |
| Invention: | | | | |
| A | 0.05 | +100 | 15.4 | 14.8–16.1 |
| | 0.005 | +44 | | |
| B | 0.05 | +83 | 9.9 | 93.–10.4 |
| | 0.005 | +44 | | |
| Prior Art: | | | | |
| X | 0.5 | +80 | 62.3 | 58.1–66.8 |
| | 0.05 | +13 | | |
| | 0.005 | +0 | | |
| Y | 0.05 | +10 | 30.0 | 27.3–33.0 |
| | 0.005 | ±0 | | |
| Z | 0.05 | +27 | 22.6 | 20.8–24.6 |
| | 0.005 | ±0 | | |

For pharmaceutical purposes the compounds of the present invention are administered to warm-blooded animals perorally, parenterally, or rectally or by the respiratory route as active ingredients in customary dosage unit compositions, that is, compositions in dosage unit form consisting essentially of an inert pharmaceutical carrier and one effective dosage unit of the active ingredient, such as tablets, coated pills, capsules, wafers, powers, solutions, suspensions, emulsions, syrups, suppositories, inhalation sprays or aerosols and the like. One effective dosage unit of the compounds according to the present invention is from 0.00083 to 8.34 μgm/kg body weight, preferably 0.0083 to 0.84 μgm/kg body weight. The daily dose rate is 0.0025 μgm/kg to 0.025 mgm/kg body weight, preferably 0.025 μgm/kg to 0.0025 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 16

Tablets

The tablet composition is compounded from the following ingredients:

| | |
|---|---|
| 11-(3'-Diethylamino-n-propyl)-6, 11-dihydro-2,6-dimethyl-5H-pyrido[2,3-b][1,5]benzodiazepin-5-one hydrochloride | 0.005 parts |
| Corn starch | 75.000 parts |
| Lactose | 49.995 parts |
| Polyvinyl pyrrolidone | 4.000 parts |
| Magnesium stearate | 1.000 parts |
| Total | 130.000 parts |

Preparation

The corn starch and the lactose are intimately admixed, and the mixture is homogeneously moistened with an aqueous solution of the pyridobenzodiazepinone and polyvinyl pyrrolidone. The moist mass is granulated through a 1.5 mm-mesh screen, dried at 45° C. and again passed through the screen. The dry granulate thus obtained is mixed with the magnesium stearate, and the composition is compressed into 130-mgm tablets in a conventional tablet making machine. Each tablet is an oral dosage unit composition containing 5 μgm of the pyridobenzodiazepinone compound.

EXAMPLE 17

Coated pills

The pill core composition is compounded from the following ingredients:

| | |
|---|---|
| 11-(3'-Diethylamino-n-propyl)-6, 11-dihydro-2,6-dimethyl-5H-pyrido[2,3-b][1,5]benzodiazepin-5-one hydrochloride | 0.05 parts |
| Calcium acid phosphate, anhydrous | 34.00 parts |
| Corn starch | 9.95 parts |
| Gelatin | 2.00 parts |
| Talcum | 4.00 parts |
| Total | 50.00 parts |

Preparation

The pyridobenzodiazenpinone is intimately admixed with the corn starch and the calcium acid phosphate, and the mixture is moistened with an aqueous solution of the gelatin and granulated through a 1.5 mm-mesh screen, dried at 45° C. and again passed through the screen. The dry granulate thus obtained is admixed with the talcum, and the composition is compressed into 50 mgm-pill cores, which are then coated with a thin sheel consisting essentially of a mixture of sugar and talcum and finally polished with beeswax. Each coated pill is an oral dosage unit composition containing 50 μgm of the pyridobenzodiazepinone compound.

EXAMPLE 18

Gelatin capsules

The capsule filler composition is compounded from the following ingredients:

| | |
|---|---:|
| 11-(3'-Diethylamino-n-propyl)-6, 11-dihydro-2,6-dimethyl-5H-pyrido[2,3-b][1,5]benzodiazepin-5-one hydrochloride | 0.002 parts |
| Corn starch | 79.998 parts |
| Colloidal silicic acid | 3.000 parts |
| Magnesium stearate | 2.000 parts |
| Total | 85.000 parts |

Preparation

An aqueous solution of the pyridobenzodiazepinone salt is sprayed onto the colloidal silicic acid, the mixture is dried and intimately admixed with the other ingredients, and 85 mgm-portions of the composition are filled into gelaatin capsules of suitable size. Each capsule is an oral dosage unit composition containing 2 μgm of the pyridobenzodiazepinone salt.

EXAMPLE 19

Suppositories

The suppository composition is compounded from the following ingredients:

| | |
|---|---:|
| 11-(3'-Diethylamino-n-propyl)-6, 11-dihydro-2,6-dimethyl-5H-pyrido[2,3-b][1,5]benzodiazepin-5-one hydrochloride | 0.02 parts |
| Suppository base (e.g. cocoa butter) | 1699.98 parts |
| Total | 1700.00 parts |

Preparation

The suppository base is melted and cooled to 38° C., the milled pyridobenzodiazepinone salt is homogeneously dispersed therein, the mixture is cooled to 35° C. and 1700 mgm portions thereof are poured into cooled suppository molds and allowed to harden therein. Each suppository is a rectal dosage containing 20 μgm of the pyridobenzodiazepione salt.

EXAMPLE 20

Solution

The solution is compounded from the following ingredients:

| | |
|---|---:|
| 11-(3'-Diethylamino-n-propyl)-6, 11-dihydro-2,6-dimethyl-5H-pyrido[2,3-b][1,5]benzodiazepin-5-one hydrochloride | 0.0001 parts |
| Carboxymethyl cellulose | 0.1 parts |
| Methyl p-hydroxy-benzoate | 0.05 parts |
| Propyl p-hydroxy-benzoate | 0.01 parts |
| Cane sugar | 10.00 parts |
| Glycerin | 5.0 parts |
| Sorbitol solution, aqueous, 70% | 20.0 parts |
| Flavoring | 0.3 parts |
| Distilled water c.s.ad | 100.0 parts by vol. |

Preparation

The distilled water is heated to 70° C., and the p-hydroxybenzoates, the glycerin and carboxymethyl cellulose are dissolved therein, while stirring. The solution is cooled to room temperature, and the pyridobenzodiazepinone salt is added while stirring and dissolved therein. After addition of the sugar, sorbitol solution and flavoring, the solution is evacuated for de-aeration while stirring. The solution is an oral dosage unit composition, 5 ml of which contain 5 μgm of the pyridobenzodiazepinone salt.

EXAMPLE 21

Aerosol

The aerosol is compounded from the following ingredients:

| | |
|---|---:|
| 11-(3'-Diethylamino-n-propyl)-6, 11-dihydro-2,6-dimethyl-5H-pyrido[2,3-b][1,5]benzodiazepin-5-one hydrochloride | 0.75 parts |
| Ethanol | 1,004.25 parts |
| Propellant mixture | 8,895.00 parts |
| Total | 9,900.00 parts |

Preparation

The pyridobenzodiazepinone salt is dissolved in the ethanol, the solution is cooled to −30° C. and filled into correspondingly cooled aerosol cans, the propellant mixture at −50° C. is added, and the cans are closed with a metering valve which expels a quantity of aerosol containing 0.005 mgm of the pyridobenzodiazepinone salt with each actuation. The aerosol is an inhalation dosage unit composition.

Any one of the other pyridobenzodiazepiones embraced by formula I or a non-toxic, pharmacologically acceptable acid addition salt thereof may be substituted for the particular pyridobenzodiazepinone salt in Examples 16 through 21. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

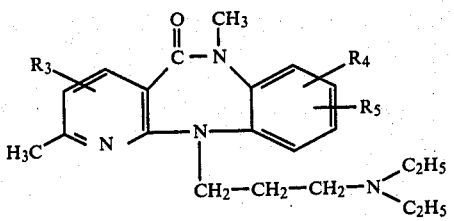

wherein $R_3$, $R_4$ and $R_5$ are each hydrogen or methyl, or a non-toxic, pharmacologically acceptable acid addition salt thereof.

2. A compound of claim 1, which is 11-(3-Diethylamino-propyl)-6,11-dihydro-2,6-dimethyl-5H-pyrido[2,3-b][1,5]-benzodiazepin-5-one or a non-toxic, pharmacologically acceptable acid addition salt thereof.

3. A compound of claim 1, which is 11-(3-Diethylamino-propyl)-6,11-dihydro-2,6,8,9-tetramethyl-5H-pyrido[2,-3-b][1,5]benzodiazepin-5-one or a non-toxic, pharmacologically acceptable acid addition salt thereof.

4. A bronchospasmolytic and bronchosecretolytic pharmaceutical dosage unit composition consisting essentially of an inert pharmaceutical carrier and an effective bronchospasmolytic and bronchosecretolytic amount of a compound of claim 1.

5. The method of relieving bronchial asthma in a warm-blooded animal in need thereof, which comprises administering to said animal an effective bronchospasmolytic and bronchosecretolytic amount of a compound of claim 1.

* * * * *